United States Patent
Duerksen-Hughes et al.

(10) Patent No.: US 7,439,015 B2
(45) Date of Patent: Oct. 21, 2008

(54) METHODS FOR DETECTING DNA VIRUSES

(75) Inventors: Penelope J. Duerksen-Hughes, Redlands, CA (US); Maria Filippova, Riverside, CA (US); Istvan Fodor, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 95 days.

(21) Appl. No.: 11/008,488

(22) Filed: Dec. 8, 2004

(65) Prior Publication Data

US 2006/0057600 A1    Mar. 16, 2006

Related U.S. Application Data

(60) Provisional application No. 60/528,438, filed on Dec. 8, 2003.

(51) Int. Cl.
- *C12Q 1/70* (2006.01)
- *C12Q 1/66* (2006.01)
- *C12Q 1/02* (2006.01)
- *C12N 7/00* (2006.01)
- *C12N 15/00* (2006.01)

(52) U.S. Cl. ............ 435/5; 435/8; 435/29; 435/235.1; 435/320.1; 435/455

(58) Field of Classification Search ............ None
See application file for complete search history.

(56) References Cited

U.S. PATENT DOCUMENTS

| | | | | |
|---|---|---|---|---|
| 5,155,020 | A | 10/1992 | Paoletti | 435/69.1 |
| 5,382,425 | A | 1/1995 | Cochran et al. | 435/69.1 |
| 5,418,132 | A | 5/1995 | Olivo | 435/5 |
| 5,591,579 | A | 1/1997 | Olivo et al. | |
| 5,939,253 | A | 8/1999 | Scholl et al. | 435/5 |
| 6,136,538 | A | 10/2000 | Olivo et al. | |
| 6,270,958 | B1 | 8/2001 | Olivo et al. | 435/5 |
| 6,326,480 | B1 | 12/2001 | Kovelman et al. | 536/23.1 |
| 6,699,657 | B2 | 3/2004 | King et al. | 435/5 |

FOREIGN PATENT DOCUMENTS

| | | |
|---|---|---|
| GB | 2321103 A | 7/1998 |
| WO | WO01/87350 A2 | 11/2001 |

OTHER PUBLICATIONS

Baldick, et al. Mutational Analysis of the Core, Spacer and Initiator Regions of Vaccinia Virus Intermediate-Class Promoters. J. Virol. 1992 66(8):4710-4719.*

(Continued)

*Primary Examiner*—Mary E. Mosher
*Assistant Examiner*—Stuart W Snyder
(74) *Attorney, Agent, or Firm*—David A. Farah; Michael Fedrick; Sheldon Mak Rose & Anderson

(57) ABSTRACT

A DNA virus in a sample is detected by contacting the sample with host cells that have been transiently transfected with a reporter sequence under the control of a virus-specific promoter, and then detecting the reporter.

23 Claims, 1 Drawing Sheet

OTHER PUBLICATIONS

Figure 1:
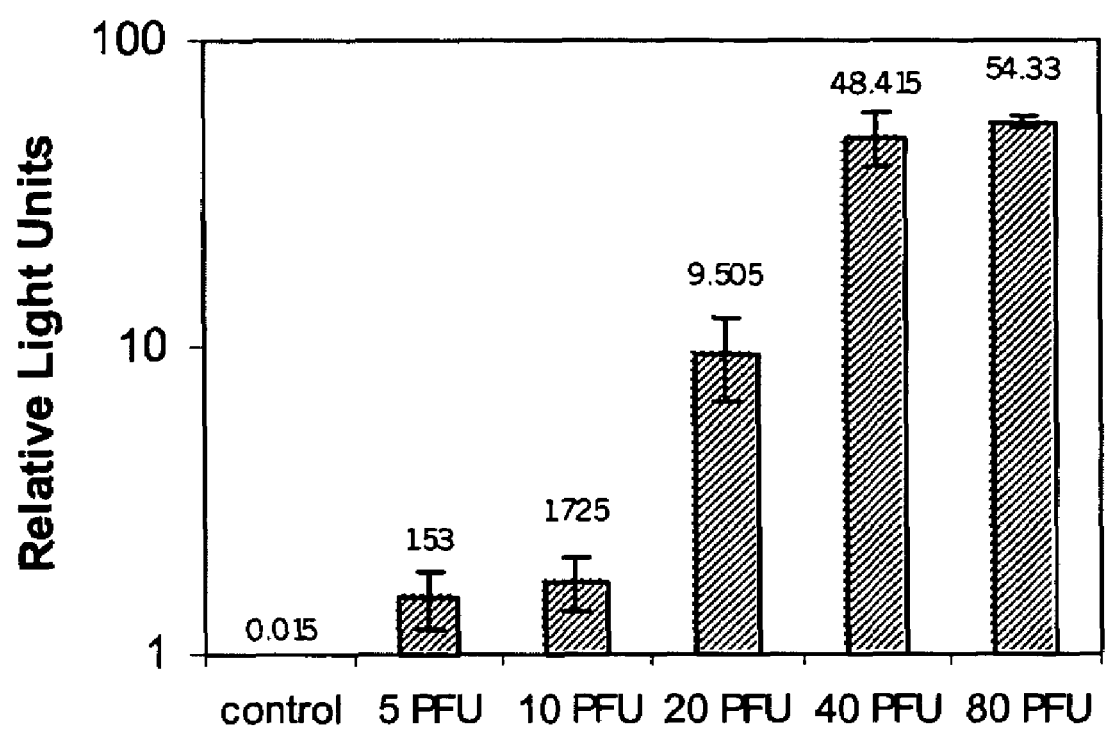

Piounaki, et al. Rapid phenotypic drug susceptibility assay for HIV-1 with a CCR5 expressing indicator cell line. J. Virol Met. 2000 vol. 85 p. 151-161.*

Neumann, et al. Gene transfer into mouse lyoma cells by electroporation in high electric fields. EMBO J. 1981 . . . 1(7):841-845.*

Chakrabarti, et al. Compact, Synthetic, Vaccinia Virus Early/Late Promoter for Protein Expression. Biotechniques. 1997 vol. 23:1094-1097.*

Miller, et al., Application of PCR to Multiple Specimen Types for Diagnosis of Cytomegalovirus Infection: Comparison with Cell Culture and Shell Vial Assay. J Clin Microb. 1994. 32(1):5-10.*

Gnant, et al., Tumor-Specific Gene Delivery Using Recombinant Vaccinia Virus in a Rabbit Model of Liver Metastases. J NCI 1999. 91(20):1744-1750.*

Ober, et al. Immunogenicity and Safety of Defective Vaccinia Virus Lister: Comparison with Modified Vaccinia Virus Ankara. J Virol. 2002; 76(15): 7713-7723.*

The International Search Report for International Application No. PCT/US2004/041455.

The Written Opinion of the International Searching Authority of the PCT for International Application No. PCT/US2004/041455.

Andreas Nitsche et al., Detection of Orthopoxvirus DNA by Real-Time PCR and Identification of Variola Virus DNA by Melting Analysis; Journal of clinical Microbiology, vol. 42, No. 2, Mar. 2004, p. 1207-1213.

Paul D. Olivo, Transgenic Cell Lines for Detection of Animal Viruses, Clinical Microbiology Reviews, vol. 9, No. 3, Jul. 1996, p. 321-334.

Y. Malpiece, et al., The gene S promoter hepatitis B virus confers constitutive gene expression, Nucleic Acids Research, vol. 11, No. 13, 1983, p. 4645-4654.

Seeger C. et al. Abstract, Biochemical and genetic evidence for the hepatitis B virus replication strategy, Science Apr. 25, 1986;232(4749):477-84.

Moolla N. et al. Abstract, Regulatory elements of hepatitis B virus transcription, J. Viral Hepat. Sep. 2002;9)5):323-31.

Kramvis A., et al. Abstract, The core promoter of hepatitis B virus, J. Viral Hepat. Nov. 1999:6(6):415-27.

*Fields Virology*, Third Edition edited by B.N .Fields, D.M. Knipe, P.M. Howley, et al.; Lippincott—Raven Publishers, Philadelphia 1996; Chapter 83 Poxviridae: The Viruses and Their Replication, Bernard Moss.

*BioTechniques* 23: 1094-1097 (Dec. 1997) Compact, Synthetic, Vacinia Virus Early/Late Promoter for Protein Expression, Sekhar Chakrabarti, Jerry R. Sisler and Bernard Moss.

A. Colosimo; K.K. Gonez; A.R. Holmes; K. Kunzelmann; G. Novelli; R.W. Malone; M.J. Bennett; D.C. Gruenert, BioTechniques 29:314-331 (Aug. 2000) Transfer and Expression of Foreign Genes in Mammalian Cells.

Andrew J. Davison; Bernard Moss, J. Mol. Biol. (1969) 210, 749-769, Structure of Vaccinia Virus Early promoters.

W.C. Fick; G.J. Viljoen, Arch. Virol (1999) 144: 1229-1239, Identification and characterisation of an early/late bi-directional promoter of the capripoxvirus, lumpy skin disease virus.

Manueal Lopez-Cabrera; John Letovsky; Ke-Qin Hu; Aleem Siddiqui, Proc. Natl. Acad. Sci. USA, vol. 87, pp. 5069-5073, Jul. 1990 Biochemistry, Multiple liver-specific factors bind to the hepatitis B virus core/pregenomic promoter: Trans-activation and repression by CCAAT/enhancer binding protein.

C. Macaulay; G. McFadden, Virology 172, 237-246 91989), Tumorigenic Poxviruses: Characterization of an Early Promoter from Shope Fibroma Virus.

Elaine Schenborn; Debyra Groskreutz, Molecular Biotechnology 1999 vol. 13, pp. 29-44, Review, Reporter Gene Vectors and Assays.

V. Srinivasan; W.M. Schnitzlein; D.N. Tripathy, Avian Diseases 47:286-295, 2003, A Consideration of Previously Uncharacterized Fowl Poxvirus Unidirectional and Bidirectional Late Promoters for Inclusion in Homologous REcombinant Vaccines.

World Health Organization Department of Communicable Disease Surveillance and Response, WHO Advisory Committee on Variola Virus Research, Report of the second meeting, Geneva, Switzerland Feb. 15-16, 2001.

Chiou-Hwa Yuh; Yuh-Long Chage; Ling-Pai Ting, Journal of Virology, Jul. 1992, p. 4073-4084, Transcriptional Regulation of Precore and Pregenomic RNAs of Hepatitis B Virus.

Michelle E. D. Martin, et al., "Identification of a Transactivating Function Mapping to the Putative Immediate-Early Locus of Human Herpesvirus 6", Journal of Virology, Oct. 1991. p. 5381-4390, vol. 64, No. 10.

* cited by examiner

METHODS FOR DETECTING DNA VIRUSES

The present application claims priority from U.S. Provisional Patent Application No. 60/528,438, filed Dec. 8, 2003, entitled "METHOD FOR THE DETECTION OF BIOLOGICAL AGENTS," the entire disclosure of which is hereby incorporated by reference.

BACKGROUND

Rapid and accurate methods are needed to detect agents which might be used in a bioterrorist attack, particularly "Category A" agents. Category A agents, as defined by the U.S. Centers for Disease Control and Prevention (CDC), include organisms that pose a public health risk because they can be easily disseminated or transmitted from person to person and that result in high mortality rates. Smallpox, a Category A agent, is considered to be a particularly dangerous threat, as fatality rates could be higher than 25% from exposure to the smallpox virus.

Earlier methods for detecting DNA viruses like the smallpox virus involve the time-consuming process of growing viable virus particles from a sample potentially containing the virus. More recent PCR- or antibody-based methods are potentially very rapid and sensitive, and can possibly be incorporated into portable devices. However, it is necessary to know enough about the viral agent of interest to design appropriate primers or to generate an antibody in order to use such methods. This means that a viral agent could be genetically engineered, or could naturally mutate, such that its genome or proteins would not be detected by these methods. In addition, PCR- and antibody-based assays do not distinguish between viable, infectious agents and non-viable or inactivated agents.

SUMMARY

The present methods allow the detection of viable, infectious DNA viruses in a sample. In one embodiment, the present methods determine whether a DNA virus is present in a sample by contacting the sample with a first group of host cells capable of being infected by the DNA virus and transiently transfecting the host cells with a reporter construct. The reporter construct comprises a reporter sequence operably linked to a virus-specific promoter sequence that enhances the transcription of the reporter sequence when the host cell is infected by the DNA virus to be detected. The present method further includes the step of determining an expression level of the reporter sequence in the host cells, thereby determining whether the DNA virus is present in the sample. Transient transfection can be accomplished by transduction, electroporation, heat shock, or lipofection.

The present methods are particularly advantageous for detecting cytoplasmic-replicating DNA viruses, including those of the Poxviridae family such as vaccinia and variola (smallpox), in which case the promoter sequence can be the sequence of SEQ ID NO. 1. The present methods can also be used to detect viruses of the Hepadnaviridae family, such as the hepatitis B virus, as well as those of the Herpesviridae family such as Herpes simplex, Cytomegalovirus, and Epstein-Barr virus. Such viruses can be detected, e.g., in samples comprising tissue from a human or non-human animal subject, such as blood, plasma, cerebrospinal fluid, or saliva. Alternatively, the sample can be derived from a subject treated with a therapeutic viral construct.

In some embodiments, the virus-specific promoter used in the present methods enhances the transcription of the reporter sequence in the presence of a plurality of DNA viruses, generally viruses from the same family. This embodiment is advantageous when a positive control assay is performed together with the present methods. The positive control assay includes the steps of transiently transfecting a second group of host cells with the reporter construct, infecting the second group of host cells with a second DNA virus, and then determining an expression level of the reporter sequence in the second group of host cells, thereby determining that the presence of the DNA virus of interest in the sample can be detected.

In another embodiment, the present methods determine whether a poxvirus is present in a sample. In this embodiment, host cells capable of being infected by a poxvirus are contacted with a sample and transiently transfected with a reporter construct. The reporter construct comprises a reporter sequence operably linked to a poxvirus-specific promoter sequence. The expression level of the reporter sequence in the host cells is then determined, thereby determining whether the poxvirus is present in the sample. The promoter sequence used in this embodiment can be, for example, any of SEQ ID NO. 1, SEQ ID NO. 2, SEQ ID NO. 3, or SEQ ID NO. 4. This embodiment can further comprise the step of comparing the expression level of the reporter sequence to a calibration curve in order to quantitatively determine the amount of poxvirus in the sample, where the data points on the calibration curve are determined by contacting samples having a known titer of the poxvirus with respective groups of host cells capable of being infected by the poxvirus, transiently transfecting the host cells with a reporter construct comprising a reporter sequence operably linked to a poxvirus-specific promoter sequence, and determining an expression level of the reporter sequence in each of the groups of host cells.

DRAWINGS

These and other features, aspects and advantages of the present invention will become better understood with regard to the following description, appended claims, and accompanying figures where:

FIG. 1 is a graph depicting the results of an experiment in which different titers of vaccinia virus were detected using the present method.

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by their intended use.

DESCRIPTION

Definitions

As used herein, the following terms have the meanings given below, unless a different meaning is clearly intended by the context in which such term is used.

"Cytoplasmic-replicating DNA virus" refers to a virus which stores genetic information at least partially in deoxyribonucleic acid (DNA) and which transcribes such genetic information outside the nucleus of a host cell which it infects, i.e. in the cytoplasm of a host cell. Cytoplasmic-replicating DNA viruses include viruses of the Poxyiridae family.

"E/L promoter" refers to a synthetic early-late pox virus promoter described in Chakrabarti, S., Sisler, J. R., and Moss, B., "Compact, synthetic, vaccinia virus early/late promoter for protein expression," *BioTechniques*, 23:1094-1097 (1997) and having the sequence AAAAATTGAAATTT-TATTTTTTTTTTGGAATATAAATA (SEQ ID NO. 1).

"Expression" of a nucleotide sequence refers to the transcription of the sequence and its subsequent translation into a polypeptide.

"Expression level," with reference to a reporter sequence (as defined below), refers to the abundance of the reporter sequence. The abundance of a reporter corresponding to the reporter sequence is normally detected in the present methods as a proxy for the expression level of the reporter sequence, and determining the expression level of a reporter sequence can comprise determining the abundance of the corresponding reporter in a host cell or group of host cells.

An "expression vector" is a nucleic acid construct, generated recombinantly or synthetically, comprising DNA or other nucleic acids able to be recognized and transcribed by viral and cellular transcription factors in a host cell, in particular the transcription factors of a virus to be detected by the present methods. The expression vector can be, for example, part of a plasmid or virus.

"Host cell" refers to a eukaryotic cell capable of being infected with a virus in an assay according to the present methods.

"Nucleotide sequence" refers to a chain of deoxyribonucleotides or ribonucleotides, i.e. oligonucleotides or polynucleotides, in either single- or double-stranded form.

The term "operably linked" refers to functionally related nucleic acid sequences. When a promoter controls and/or enhances the transcription of a nucleotide sequence, it is said to be operably linked to the nucleotide sequence.

"Promoter" refers to a nucleotide sequence or sequences, usually comprising a transcription factor binding site, that directs and/or enhances transcription of another nucleotide sequence.

"Reporter sequence" refers to a nucleotide sequence which can be transcribed and detected, or whose polypeptide translation product can be detected, such as by spectroscopic, photochemical, biochemical, immunochemical, luminescence, or chemical means. "Reporter construct" refers to an expression vector comprising a reporter sequence operably linked to a promoter. "Reporter" refers to a polypeptide translation product of a reporter sequence.

"Transfection" refers to a process by which exogenous nucleotide sequences, typically DNA, enter a recipient host cell. For purposes of the present methods, transfection includes processes in which nucleotide sequences are physically or chemically transferred into a cell, such as through electroporation or lipofection, as well as virally mediated processes, i.e. transduction. "Transient transfection" refers to methods of transfection in which the exogenous DNA is not stably incorporated into the recipient host cell's chromosomal DNA and functions for only a limited time. Transiently transfected DNA is generally located predominantly within a cell's cytoplasm.

"Virus-specific promoter" refers to a promoter that directs and/or enhances transcription of another nucleotide sequence only in the presence of transcription factors or other proteins encoded by a particular virus or by a limited number of viruses of a particular genus or family.

As used herein, the term "comprise" and variations of the term, such as "comprising" and "comprises," are not intended to exclude other additives, components, integers or steps.

Methods

The present methods are cell-based assays which allow the detection of DNA viruses, in particular cytoplasmic-replicating DNA viruses. Prior art cell-based assays for detecting DNA viruses involved the creation of cells which were stably transfected with a reporter sequence under the control of a promoter specific to that virus, such that the promoter and reporter sequences were incorporated into a host cell's chromosomal DNA. This approach suffers from the tendency of reporter sequences in the nuclei of such stably transfected cells to be silenced over time, so that they are no longer transcribed in the presence of the appropriate transcription factors.

In the present methods, host cells are transiently transfected with a reporter construct, so that there is little opportunity for gene silencing to occur. Many more copies of a reporter sequence can also be placed into a cell using transient transfection, thus increasing the sensitivity of the present methods. With respect to cytoplasmic-replicating DNA viruses, transient transfection has the additional advantage of locating reporter constructs predominantly at the site of viral genome transcription, i.e. in the cytoplasm of the host cell, which further increases the sensitivity of the present assay.

To detect the presence of viable, infectious DNA viruses according to the present methods, host cells are placed into contact with a sample. The sample can be any sample suspected of containing a virus of interest. In one embodiment, the sample comprises tissue or fluid (such as blood, plasma, cerebrospinal fluid or saliva) derived from a human or animal subject. The sample can also be derived from an inanimate source, such as a liquid or solid particulate sample gathered from the environment, e.g. from the surface of an object. The sample should be in a condition that does not substantially interfere with the growth or metabolism of the host cells, however. For example, it should be at a temperature conducive to cellular viability and growth, and should not comprise substances that would kill host cells or inhibit the cellular mechanisms needed by a virus of interest to replicate in the host cells.

In addition to contacting a group of host cells with a sample, additional groups of host cells are preferably exposed to other conditions in order to conduct negative and positive control assays. In order to verify that the carrier substance used to gather the sample and/or the growth medium used to grow the host cells does not contain a virus of interest, a negative control assay is performed. In the negative control assay, a group of host cells is contacted with the carrier and/or the growth medium instead of with the sample, and an assay as described herein is then conducted.

A positive control assay, using host cells exposed to a solution known to contain a specified amount of an appropriate virus, is also preferably performed in the present methods. The virus used as a positive control can be the same virus as the virus of interest to be detected, or can be another virus capable of effecting the transcription of a reporter sequence that is transiently transfected into the host cells. In a preferred embodiment, the virus used in the positive control assay is a different virus which is less infectious to humans and/or is less virulent than the virus to be detected in the present methods. Most commonly, the virus used in the positive control assay is from the same genus or family as the virus to be detected. For example, vaccinia virus can be used as a positive control for a smallpox assay as described herein, as long as the promoter in the reporter construct allows expression by both smallpox and vaccinia transcription factors. If the virus to be detected is highly infectious and/or virulent, such as smallpox virus, the use of less infectious or virulent viruses in the positive control assay has the advantage of reducing the risk to technicians conducting the present assay.

Host cells should be capable of being infected by the virus of interest as well as by a virus used as a positive control, if a different virus is used for the positive control assay. Host cells should also have the ability to express the reporter sequence and/or the reporter at easily detectable levels when infected by the virus of interest. Preferably, host cells are used which plate such that they are significantly confluent, such as 50%-70% confluent, at the time of the assay. A majority of host cells are also preferably in log phase when exposed to the sample to be tested, i.e. are growing at a relatively constant and generally exponential rate. Depending on the method of analysis to be used, host cells can be plated on glass cover slips or can be directly plated into plastic wells for convenience.

Using the foregoing criteria, one of skill in the art can choose an appropriate host cell to use in the present methods. When detecting DNA viruses capable of infecting humans, human or other mammalian cell lines are preferred. For example, the host cells can be U2OS cells, derived from human osteosarcoma cells, CV-1 monkey kidney cells, Chinese hamster ovary (CHO) cells, or baby hamster kidney (BHK) cells.

Host cells are preferably transiently transfected with a reporter construct in the present methods after an appropriate amount of time following exposure of the host cells to a sample, i.e. sufficient time to allow infection of the host cells to occur. When assaying for the presence of poxviruses, between approximately 30 and 60 minutes is generally a sufficient period of time. Transfection of host cells following contact with a sample (and any viruses contained therein) is preferred, as viral infection of such cells is believed to facilitate the transfer of the reporter construct into the cells.

Host cells can alternatively be transfected just prior to contact with a sample. In this embodiment, transfected host cells are preferably placed into contact with a sample as soon after transfection as is practicable, generally within about a week and/or within about 10-15 cell divisions. Preferably, transfected host cells are exposed to a sample within 96 hours post-transfection and/or within 4-8 cell divisions. When a viral vector is used to transfect the host cells, the viral vector can be contacted with the host cells at the same time as a sample is placed into such contact.

Transient transfection can be accomplished in any manner known to the art, including infection with a viral vector, electroporation, heat shock, and lipofection. In one embodiment, the method of transfection used is lipofection, which can be performed for example with the FuGENE 6 Transfection Reagent (available from Roche Diagnostics Corporation, Roche Applied Science, P.O. Box 50414, 9115 Hague Road, Indianapolis, Ind.). In another embodiment, the assay is performed as a co-infection model, by the insertion of the reporter construct into a viral vector, such as an adenovirus or retrovirus construct. An advantage of the adenovirus-based approach is that high levels of the reporter sequence can be carried into the cytoplasm of a host cell, increasing the sensitivity of the assay. Transient transfection can also be accomplished through the use of a gene gun, such as the Helios Gene Gun System (available from Bio-Rad Laboratories, Hercules, Calif.), which bombards cells with particles (typically gold particles) coated with nucleic acids.

In addition to transfecting a reporter construct, expression vectors comprising positive and negative controls are also preferably transfected into groups of host cells that have been placed in contact with the sample of interest. An expression vector serving as a negative control can comprise, for example, the reporter sequence used in the reporter construct that is not operably linked to a promoter. A positive control can comprise, e.g., the same reporter sequence operably linked to a strong, constitutive promoter in the host cells, such as a CMV promoter.

The promoter used in the reporter construct in the present methods is specific to the virus of interest or to a limited group of viruses of the same genus or family, so that the reporter will be expressed in the presence of such virus or viruses. The promoter can also be specific to a stage of the life cycle of a virus or to the expression of a particular viral gene. In a preferred embodiment, a promoter is used which is active at different stages of the life cycle of a virus, in order to increase the expression level of the reporter sequence and hence the sensitivity of the assay.

Reporters used in the present assay are detectable moieties known to those of skill in the art. Examples of reporters include Green Fluorescent Protein (GFP), luciferase, beta-galactosidase, and secreted alkaline phosphatase (SEAP). In a preferred embodiment, the reporter gene is Enhanced Green Fluorescent Protein (EGFP), which is a version of GFP that has been optimized for brighter fluorescence and higher expression in mammalian cells. In embodiments of the present assay used to quantitatively measure the presence of a DNA virus in a sample, the reporter is preferably luciferase.

The method of measuring a reporter depends on the reporter used, as will be understood by those of skill in the art. For example, expression of EGFP can be measured by inverted fluorescence microscopy, using an instrument such as a Leica fluorescence stereo microscope (available from Leica Microsystems, Wetzlar, Germany) equipped with a mercury 100 W lamp power supply connected to a CCD camera. In this case, measurements are preferably taken approximately twenty-four hours following transient transfection of the EGFP sequence into host cells contacted with a sample. Fluorescence emitted from cells in a 96-well plate can also be measured with a microplate fluorimeter (such as the FL600 Fluorescent Microplate Reader available from Bio-Tek Instruments, Inc., Highland Park, P.O. Box 998, Winooski, Vt.). When the reporter is detectable through fluorescence, the expression level of the reporter can be expressed as (magnitude of test fluorescent signals)/(magnitude of reference fluorescent signals), where the reference signals can, for example, be derived from a negative control assay or a number of aggregated negative control assays.

In another embodiment, measurement of the reporter can be performed using flow cytometry, using an instrument such as the BD FACSCaliber System (available from BD Biosciences, 1 Becton Drive, Franklin Lakes, N.J.). In another embodiment, such as when the reporter is EGFP, measurement can be performed by immunoblotting or an ELISA assay, using any of a number of commercially available antibodies specific for EGFP.

Following sample contact and transfection, the expression of the reporter sequence is measured. After measuring the abundance of the reporter sequence or the reporter, the measurements are analyzed to determine whether the virus of interest is present in the sample. The analysis can include creating controls using appropriate samples from the general population (if the sample is a tissue sample), including positive controls known to contain the virus of interest and negative controls known not to contain the virus, and using measurements taken from those samples to calculate or estimate a number of parameters in the sample, such as virus presence and titer. The sensitivity, specificity, positive predictive value and negative predictive value of the assay are preferably also calculated. These statistical analyses allow the development of criteria for determining whether a particular measurement of reporter sequence expression is likely to indicate the presence of a virus of interest in a sample.

In one embodiment, the determination of whether a particular measurement of reporter sequence expression indicates the presence of a virus of interest in a sample is made by comparing the expression level of the reporter sequence to a calibration curve. The data points on the calibration curve can be determined by first contacting samples having a known titer of the virus of interest with host cells capable of being infected by the virus, transiently transfecting the host cells with a reporter construct as described herein, and then determining the expression level of the reporter sequence in the host cells.

Results from the present methods are generally available within a matter of hours to days and are generally faster than culture-based methods, which is important when dealing with an outbreak of a contagious agent such as smallpox. Further, the present methods can distinguish between the presence of viable, infectious agents and non-viable or inactivated material. Additionally, the present methods are less susceptible to false negative results due to genetic engineering or mutations when compared with antibody or PCR-based methods. Since the methods of the present invention are cell-based, they are suitable for use in hospitals or other facilities with laboratory capabilities. Additionally, the present methods can be easily automated using available robotic equipment for high throughput analysis, as will be understood by those of skill in the art.

The present methods can, in addition to detecting viral contagions, be used to monitor human or non-human animal subjects treated with a therapeutic viral construct based on a DNA virus which is administered in the course of a gene therapy regimen. The sample in this case would comprise tissue from such a subject, and the assay would be used to detect the presence of infectious virus particles in the sample.

Promoters

DNA virus promoters known to the art can be used in the present methods. When the presence of a particular virus is to be assayed, a promoter that is specific to that virus, or which is specific to a limited number of viruses of a particular genus or family, is chosen for use. It is preferred that viral promoters having no significant homology with promoters in the host cell nucleus be used, in order to minimize background expression and decrease the incidence of false positives.

The present methods are particularly advantageous for the detection of poxviruses. Poxviruses shut off transcription of cellular genes in order to maximize production of their own proteins, and as a result, transcription of viral genes and translation of virus proteins is much higher (up to and beyond 1000-fold) than are those of the host cell. When the virus to be detected is smallpox, smallpox or vaccinia promoters are preferably selected. The smallpox virus has three classes of promoters, which are active, respectively, in the early, intermediate, and late stages of replication. A comparison of the sequences of these three classes of smallpox virus promoters is shown in Table 1 below (with noncritical nucleotides designated with an "N").

TABLE 1

|  | Core |  | Initiator |  |
|---|---|---|---|---|
| Early | AAAANTGAAANNNTA | (SEQ ID NO.2) | A/G |  |
|  | or |  |  |  |
|  | AAAANTNGAAANNNTA | (SEQ ID NO.3) |  |  |
| Intermediate | TNNNTTNAAANNAA | (SEQ ID NO.4) | TAAA | (SEQ ID NO.5) |
| Late | A/T-rich |  | TAAATG/A | (SEQ ID NO.6) |

The present methods can make use of naturally occurring promoters, such as those shown in Table 1, or alternatively can make use of a synthetic poxvirus-specific promoter to control expression of a reporter gene. A synthetic promoter that contains elements of both the early and late promoters, the E/L promoter, responds to poxviruses (including vaccinia and variola) at different stages of the viral life cycle. The use of such a promoter increases the sensitivity of the present assay and detects poxviruses throughout their life cycle. This promoter has no significant homology with promoters in mammalian host cells. The use of a promoter like the E/L promoter which is active with both smallpox and vaccinia viruses has the additional advantage of allowing the use of a vaccinia virus in the positive control assay rather than smallpox virus.

When detecting viruses of the Hepadnaviridae family, any of the four types of promoters identified for such viruses, i.e. the core, S1, S2 and X promoters, or any combination thereof can be used (see, e.g., Kramis and Kew, *J. Viral Hepat.*, 6:415-427 (1999); Moolla, N. et al, *J. Viral Hepat*, 9:323-331 (2002); Malpiece et al., "The Gene S Promoter of Hepatitis B Virus Confers Constitutive Gene Expression", Nucleic Acids Res., 11:4645-4654 (1983)). The core promoter directs the synthesis of mRNA which serves as a template for the synthesis of core and polymerase proteins. The S1, S2 and X promoters of viruses of the Hepnaviridae family direct the synthesis of specific gene products. Enhancers of such promoters which direct liver-specific and differentiation state-specific utilization of these promoters, enhancer I (ENI) and enhancer II (ENII), can also be incorporated into a reporter construct used to detect hepatitis B virus in the present methods.

When detecting hepatitis B virus using the present methods, core promoter sequences such as those shown in Table 2 below can be used.

TABLE 2

| GenBank Accession No. | Sequence | |
|---|---|---|
| AY603446 | GGGAGGAGAT TAGGTTAAAG GTCTTTGTAT TAGGAGGCTG TAGGCATAAA TTGGTCTGCG C | (SEQ ID NO. 7) |
| AY489315 | GGGGGAGGAG ATTAGGTTAA AGGTCTTTGT ATTAGGAGGC TGTAGGCATA AATTGGTCTG CGCACCAACA TCATGCAACT TTTTCACCTC TGCCTAATCA TCTCTTGT | (SEQ ID NO. 8) |
| AB099504 | GATGATTAGG CAGAGGGGAA AAAGGTGCAT GGTGCTGGTG AACAGACCAA TTTATGCCTA CAGCCTCCTA GTACAAAGAC CTTTAACCTA GTCTCCTCCC CTAACTCCTC CCAGTCTTTA AACAAACAGT CTTTGAAGTA TGCCTCAAGG TCGGTC | (SEQ ID NO. 9) |

EXAMPLE 1

Poxvirus Assay with U2OS Cells

An assay was performed to detect the presence of poxvirus in a sample. The reporter construct was made using a promoterless plasmid coding for EGFP, pEGFP1, obtained from Clontech (1020 East Meadow Circle, Palo Alto, Calif.). The E/L promoter was inserted upstream of the EGFP sequence in the plasmid's multiple cloning site. This plasmid was designated pEGFP-1 E/L.

A second expression vector was constructed from the same plasmid, pEGFP1, in order to serve as a positive control. A strong, constitutive CMV promoter was inserted into the multiple cloning site instead of the E/L promoter. This vector was designated pEGFP-1 CMV. Candidate clones were identified using restriction endonuclease digestions with enzymes expected to cut at the insertion sites, and identification of the desired products was confirmed by sequencing.

A U2OS cell line, obtainable from the American Type Culture Collection (HTB-96), was selected as the host cell line. These cells were 50%-70% confluent at the time of the assay. The U2OS cells were plated one day prior to the assay on glass cover slips in individual wells of a 6-well plate, at a density of $2.5 \times 10^5$ cells per well.

While in log stage growth, cells were exposed either to media (McCoys 5a medium supplemented with 1.5 mM L-glutamine, 90%; plus fetal bovine serum, 10%) alone as a negative control or to solutions containing the Lister strain of vaccinia virus. Cells were seeded with virus at an MOI of 1 (i.e., one virus per cell). 30 minutes after the initial infection, the cells were then transiently transfected using the FuGENE 6 Transfection Reagent. The expression vectors transfected were either pEGFP-1 (as a negative control), pEGFP-1 CMV (as a positive control) or pEGFP-1 E/L (the experimental vector).

Next, infectious vaccinia virus was detected by measuring the expression of the reporter, EGFP, by inverted fluorescence microscopy, using a Leica fluorescence stereo microscope equipped with a mercury 100 W lamp power supply that is connected to a CCD camera. Fluorescence was detected twenty-four hours following transient transfection of the reporter gene into host cells. Cells transfected with a plasmid coding for EGFP under the control of the E/L promoter exhibited strong fluorescence in the presence of vaccinia virus, as did those transfected with a plasmid coding for EGFP under the control of the CMV promoter in the absence of vaccinia virus. Only weak fluorescence was detected in the remaining wells.

EXAMPLE 2

Poxvirus Assay Using Different Viral Titers

CV-1 monkey kidney cells were plated in a 6-well microtiter plate, and the next day they were infected with vaccinia virus (strain Lister) with 10 plaque forming units (PFU) per well or 100 PFU per well, followed by transfection with a plasmid carrying the GFP gene under the control of the E/L promoter. Transfection was accomplished using a lipid-based transfection reagent, GENEPORTER Transfection Reagent (available from Gene Therapy Systems, Inc., San Diego, Calif., USA). Negative control cells were transfected with the plasmid, but not infected with vaccinia virus.

Cells were visualized using a Carl Zeiss Axiovert 100TV fluorescence microscope. No fluorescent cells were detected in the negative control wells. However, fluorescent cells were detected on day 1 in wells inoculated with either 10 or 100 PFU, and the number of fluorescent cells increased significantly in both cases by day 2.

EXAMPLE 3

Quantitative Poxvirus Assay

CV-1 cells were seeded into 96-well microtiter plates and then infected with doses of vaccinia virus comprising 5, 10, 20, 40, and 80 PFU per well. The cells were then transfected with a plasmid carrying the luciferase gene operably linked to the E/L promoter. On day 2 post-infection, cells were lysed and the bioluminescence of the extracts was measured in each well with a luminometer (detecting light intensity) in the presence of a luciferase substrate.

The results are shown in FIG. 1. All control wells containing CV-1 cells either infected with the virus, or transfected with the plasmid (but not both), emitted light at or below 0.015 RLU (Relative Light Units). Increasing titers of virus in non-control wells corresponded to higher RLU readings.

Although the present invention has been discussed in considerable detail with reference to certain preferred embodiments, other embodiments are possible. The steps disclosed for the present methods are not intended to be limiting nor are they intended to indicate that each step depicted is essential to the method, but instead are exemplary steps only. Therefore, the scope of the appended claims should not be limited to the description of preferred embodiments contained in this disclosure. All references cited herein are incorporated by reference to their entirety.

What is claimed is:

1. A method for determining whether a viable, infectious, cytoplasmic-replicating first DNA virus is present in a sample not known to contain the first DNA virus, comprising the steps of:

(a) contacting the sample with a first group of host cells capable of being infected by the first DNA virus;

(b) transiently transfecting the first group of host cells with a reporter construct comprising a reporter sequence operably linked to a virus-specific promoter sequence, wherein the virus-specific promoter sequence enhances the transcription of the reporter sequence in host cells infected by the first DNA virus;

(c) determining an expression level of the reporter sequence in the first group of host cells, thereby determining whether the first DNA virus is present in the sample; and (d) performing a positive control assay, the positive control assay comprising the steps of:

(i) transiently transfecting a second group of host cells with the reporter construct;

(ii) infecting the second group of host cells with a second DNA virus, the second DNA virus being less virulent than the first DNA virus, wherein the virus-specific promoter enhances the transcription of the reporter sequence in the presence of the second DNA virus; and (iii) determining an expression level of the reporter sequence in the second group of host cells, thereby determining that the presence of the first DNA virus in the sample can be detected.

2. A method for determining whether a viable, infectious, cytoplasmic-replicating first DNA virus is present in a sample not known to contain the first DNA virus, comprising the steps of:
(a) contacting the sample with host cells capable of being infected by the first DNA virus;
(b) transiently transfecting the host cells with a reporter construct comprising a reporter sequence operably linked to a virus-specific promoter sequence, wherein the virus-specific promoter sequence:
(i) can enhance the transcription of the reporter sequence when a host cell is infected by the first DNA virus; and
(ii) can enhance the transcription of the reporter sequence when a host cell is infected by a second DNA virus, the second DNA virus being in the same family as the first DNA virus and being less virulent than the first DNA virus; and
(c) determining an expression level of the reporter sequence in the host cells, thereby determining whether the first DNA virus is present in the sample.

3. The method of claim 2, wherein the step of transiently transfecting the host cells with the reporter construct is performed by a method selected from the group consisting of transduction, electroporation, heat shock, and lipofection.

4. The method of claim 2, wherein the first DNA virus is a member of the Poxviridae family.

5. The method of claim 4, wherein the virus to be detected is smallpox virus.

6. The method of claim 5, wherein the promoter sequence comprises a sequence according to SEQ ID NO. 1.

7. The method of claim 2, wherein step (b) occurs after step (a).

8. The method of claim 2, wherein the step of determining an expression level of the reporter sequence is performed by determining the abundance of a reporter, wherein the reporter is the translation product of the reporter sequence.

9. The method of claim 8, wherein the reporter is selected from the group consisting of Enhanced Green Fluorescent Protein (EGFP), Green Fluorescent Protein (GFP), luciferase, beta-galactosidase, and secreted alkaline phosphatase (SEAP).

10. A method for determining whether a poxvirus is present in a sample not known to contain the poxvirus, comprising the steps of:
(a) contacting the sample with host cells capable of being infected by a first poxvirus;
(b) transiently transfecting the host cells with a reporter construct comprising a reporter sequence operably linked to a poxvirus-specific promoter sequence, wherein the virus-specific promoter sequence:
(i) can enhance the transcription of the reporter sequence when a host cell is infected by the first poxvirus; and
(ii) can enhance the transcription of the reporter sequence when a host cell is infected by a second poxvirus, the second poxvirus being in the same family as the first poxvirus and being less virulent than the first poxvirus; and (c) determining an expression level of the reporter sequence in the host cells, thereby determining whether the first poxvirus is present in the sample.

11. The method of claim 10, wherein the promoter sequence comprises a sequence selected from the group consisting of SEQ ID NO. 1, SEQ ID NO.2, SEQ ID NO. 3, and SEQ ID NO. 4.

12. The method of claim 10, further comprising the step of comparing the expression level of the reporter sequence to a calibration curve in order to quantitatively determine the amount of the first poxvirus in the sample, wherein data points on the calibration curve are determined by:
(i) contacting a sample having a known titer of the second poxvirus with host cells capable of being infected by the second poxvirus;
(ii) transiently transfecting the host cells with a reporter construct comprising a reporter sequence operably linked to a poxvirus-specific promoter sequence; and
(iii) determining an expression level of the reporter sequence in the host cells.

13. The method of claim 2, wherein a positive control assay is performed, the positive control assay comprising the steps of:
(i) transiently transfecting a second group of host cells with the reporter construct;
(ii) infecting the second group of host cells with the second DNA virus; and
(iii) determining an expression level of the reporter sequence in the second group of host cells, thereby determining that the presence of the first DNA virus in the sample can be detected.

14. The method of claim 10, wherein a positive control assay is performed, the positive control assay comprising the steps of:
(i) transiently transfecting a second group of host cells with the reporter construct;
(ii) infecting the second group of host cells with the second poxvirus; and
(iii) determining an expression level of the reporter sequence in the second group of host cells, thereby determining that the presence of the first poxvirus in the sample can be detected.

15. The method of claim 10, wherein the virus to be detected is smallpox virus.

16. The method of claim 10, wherein the sample is selected from the group consisting of blood, plasma, cerebrospinal fluid, and saliva.

17. The method of claim 10, wherein step (b) occurs after step (a).

18. The method of claim 10, wherein the step of determining an expression level of the reporter sequence is performed by determining the abundance of a reporter, wherein the reporter is the translation product of the reporter sequence.

19. The method of claim 1, wherein the first DNA virus is smallpox virus.

20. The method of claim 19, wherein the second DNA virus is vaccinia virus.

21. The method of claim 2, wherein the sample is selected from the group consisting of blood, plasma, cerebrospinal fluid, and saliva.

22. The method of claim 5, wherein the second DNA virus is vaccinia virus.

23. The method of claim 15, wherein the second DNA virus is vaccinia virus.

* * * * *

SEQUENCE LISTING

<160> NUMBER OF SEQ ID NOS: 9

<210> SEQ ID NO 1
<211> LENGTH: 40
<212> TYPE: DNA
<213> ORGANISM: Variola

<400> SEQUENCE: 1
aaaaattgaa attttatttt ttttttttgg aatataaata                                40

<210> SEQ ID NO 2
<211> LENGTH: 15
<212> TYPE: DNA
<213> ORGANISM: Variola
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t

<400> SEQUENCE: 2
aaaantgaaa nnnta                                                          15

<210> SEQ ID NO 3
<211> LENGTH: 16
<212> TYPE: DNA
<213> ORGANISM: Variola
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 3
aaaantngaa annnta                                                         16

<210> SEQ ID NO 4
<211> LENGTH: 14
<212> TYPE: DNA
<213> ORGANISM: Variola
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t

<400> SEQUENCE: 4
tnnnttnaaa nnaa                                                           14

<210> SEQ ID NO 5
<211> LENGTH: 4

-continued

```
<212> TYPE: DNA
<213> ORGANISM: Variola

<400> SEQUENCE: 5 taaa                                                              4

<210> SEQ ID NO 6
<211> LENGTH: 6
<212> TYPE: DNA
<213> ORGANISM: Variola
<220> FEATURE:
<221> NAME/KEY: N
<222> LOCATION: (6)..(6)
<223> OTHER INFORMATION: N is G or A

<400> SEQUENCE: 6 taaatn                                                            6

<210> SEQ ID NO 7
<211> LENGTH: 61
<212> TYPE: DNA
<213> ORGANISM: Hepatitis B virus

<400> SEQUENCE: 7
gggaggagat taggttaaag gtctttgtat taggaggctg taggcataaa ttggtctgcg      60
c                                                                    61

<210> SEQ ID NO 8
<211> LENGTH: 108
<212> TYPE: DNA
<213> ORGANISM: Hepatitis B virus

<400> SEQUENCE: 8
gggggaggag attaggttaa aggtctttgt attaggaggc tgtaggcata aattggtctg      60
cgcaccaaca tcatgcaact ttttcacctc tgcctaatca tctcttgt                 108

<210> SEQ ID NO 9
<211> LENGTH: 156
<212> TYPE: DNA
<213> ORGANISM: Hepatitis B virus

<400> SEQUENCE: 9
gatgattagg cagaggggaa aaaggtgcat ggtgctggtg aacagaccaa tttatgccta      60
cagcctccta gtacaaagac ctttaaccta gtctcctccc ctaactcctc ccagtcttta    120
aacaaacagt ctttgaagta tgcctcaagg tcggtc                              156
```